United States Patent [19]

Detsch

[11] Patent Number: 4,509,519
[45] Date of Patent: Apr. 9, 1985

[54] ORAL ELECTRICAL TREATMENT APPARATUS AND METHOD

[76] Inventor: Steven G. Detsch, 4146 Bryan St., Oceanside, Calif. 92054

[21] Appl. No.: 420,853

[22] Filed: Sep. 21, 1982

[51] Int. Cl.³ .............................................. A61N 1/04
[52] U.S. Cl. .................. 128/419 F; 128/787; 128/799
[58] Field of Search ............... 128/419 F, 419 R, 787, 128/799

[56] References Cited

U.S. PATENT DOCUMENTS

| | | | |
|---|---|---|---|
| 4,155,363 | 5/1979 | Letchworth et al. | 128/419 R |
| 4,175,565 | 11/1979 | Chiarenza et al. | 128/419 F |
| 4,244,373 | 1/1981 | Nachman | 128/419 F |

Primary Examiner—William E. Kamm
Attorney, Agent, or Firm—Michael W. York

[57] ABSTRACT

An oral electrical treatment apparatus and method that includes contacting gingival tissue around a plurality of teeth with electrical contact members, providing means for supplying an electrical current to the electrical contact and providing means for adjusting the electrical current supplied to the electrical gingival contact members. The oral electrical treatment apparatus and method also includes means for monitoring the current received by the gingival tissue from the electrical gingival contact members. The oral electrical treatment apparatus and method permits defects and diseases in the mouth to be conveniently treated with a minimal amount of discomfort to the patient.

17 Claims, 3 Drawing Figures

ORAL ELECTRICAL TREATMENT APPARATUS AND METHOD

BACKGROUND OF THE INVENTION

When electricity was discovered it was first put to use for such purposes as communicating information and electric lighting. However, soon thereafter various attempts were made to use electricity to cure all sorts of medical problems. Some of these attempts included the application of electricity to the mouth such as the apparatus set forth in U.S. Pat. Nos. 562,878; 566,103; 569,380; and 1,389,662. However, the apparatus set forth in these patents were directed to certain types of diseases and/or treatments that would be subject to being questioned under current practice. Understandably, these treatments set forth in these patents are not currently in use.

In spite of these past apparently unsuccessful attempts, it has now been determined that oral defects and diseases can be successfully treated by applying proper electrical currents in a proper manner. For instance, it has been determined that it is possible to stimulate the growth of bone in the mouth through the proper use of the oral electrical treatment apparatus of the invention.

BRIEF DESCRIPTION OF THE INVENTION

This invention relates to electrical treatment apparatus and methods and more particularly to an electrical treatment apparatus and method for use in the mouth or oral cavity.

It is accordingly an object of the present invention to provide an oral electrical treatment apparatus and method for the treatment of oral defects and diseases.

It is an object of the present invention to provide an oral electrical treatment apparatus and method that can be used to generate bone, enhance periodontal osseous grafting procedures and tighten pathologically loosened teeth.

It is an object of the present invention to provide an oral electrical treatment apparatus and method that is easy to use.

It is an object of the present invention to provide an oral electrical treatment apparatus and method that is not tiring to the patient.

It is an object of the present invention to provide an oral electrical treatment apparatus and method that does not require prolonged treatment periods.

It is also an object of the present invention to provide an oral electrical treatment apparatus and method that utilizes a series of short treatment periods.

It is also an object of the present invention to provide an oral electrical treatment apparatus and method that are usable for individualized treatments.

It is also an object of the present invention to provide an oral electrical treatment apparatus and method that provides good electrical contact within the mouth.

It is also an object of the present invention to provide an oral electrical treatment apparatus and method in which electrical contacts can be precisely located within the mouth.

It is an object of the present invention to provide an oral electrical treatment apparatus and method in which electrical contacts are precisely located through the use of the teeth of the patient.

It is an object of the present invention to provide an oral electircal treatment apparatus and method that is capable of treating areas of the mouth adjacent a plurality of teeth.

It is also an object of the present invention to provide an oral electrical treatment apparatus and method in which areas of the mouth can be simultaneously separately treated.

It is also an object of the present invention to provide an oral electrical treatment apparatus and method that does not require the introduction of bulky or discomforting apparatus into the patient's mouth.

It is also an object of the present invention to provide an oral electrical treatment apparatus and method in which the majority of the apparatus is located outside of the patient's mouth.

It is also an object of the present invention to provide an oral electrical treatment apparatus and method in which the electricity applied to the patient's mouth can be easily monitored.

It is also an object of the present invention to provide an oral electrical treatment apparatus and method in which the electricity applied by a plurality of electrodes can be individually monitored.

It is also an object of the present invention to provide an oral electrical treatment apparatus and method that can be used by the patient without direct professional supervision.

The present invention provides oral electrical treatment apparatus including means for electrically contacting gingival tissue in a mouth and means locatable about a plurality of teeth in a mouth for locating the gingival electrical contacting means. Means are also provided for supplying an electrical current to the gingival electrical contacting means.

BRIEF DESCRIPTION OF THE DRAWINGS

The invention will be hereinafter more fully described with reference to the accompanying drawings in which.

DETAILED DESCRIPTION OF THE PREFERRED EMBODIMENT

Figure 1:
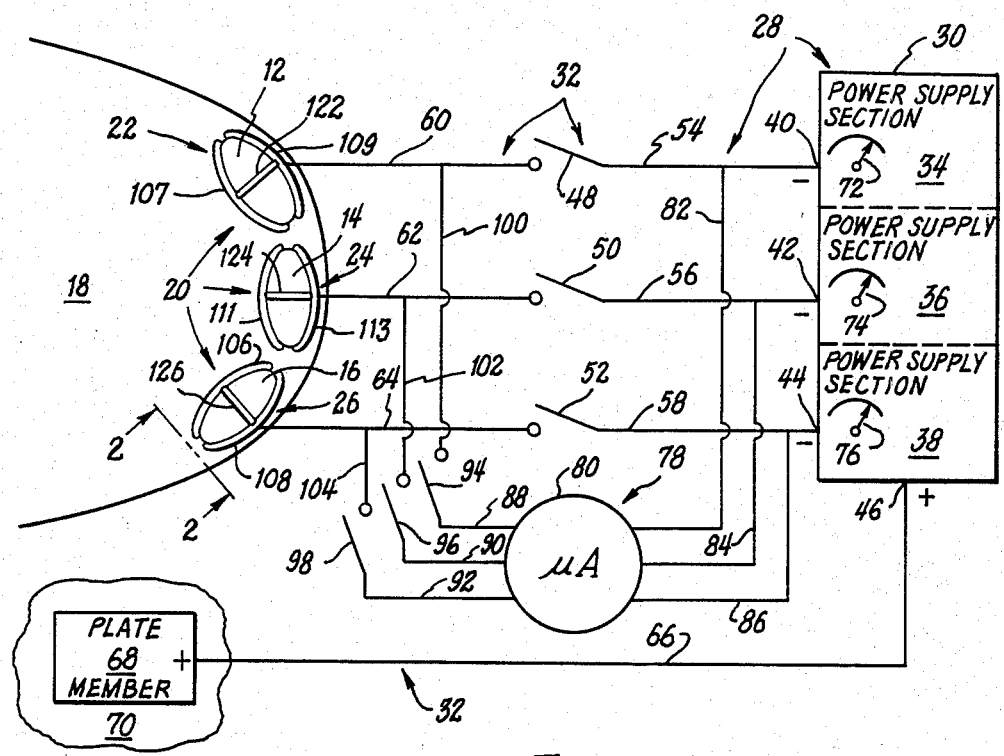
FIG. 1 is a schematic diagram illustrating the oral electrical treatment apparatus of the invention in use and connected to a patient's mouth.

Referring first to FIG. 1, the oral electrical treatment apparatus of the invention is illustrated and is designated generally by the number 10. The oral electrical treatment apparatus 10 is illustrated in use providing an electrical current to the gingival tissue surrounding the teeth 12, 14 and 16 located in the mouth 18 of a patient. The electrical treatment apparatus 10 comprises means for contacting gingival tissue in the mouth 18 designated generally by the number 20 that includes electrode assemblies 22, 24, and 26 that will be hereinafter described in further detail. The electrical treatment apparatus 10 also comprises means for supplying an electrical current to gingival contacting means designated generally by the number 28. The means for supplying an electrical current 28 includes a power supply 30 and electrical connection means designated generally by the number 32.

The power supply 30 comprises three separate substantially identical sections 34, 36 and 38 that each have the respective negative or cathode connections or outputs designated respectively by the numbers 40, 42 and 44. The power supply 30 also has a positive output or connection 46. The respective negative terminals 40, 22 and 44 are connected to respective switches 48, 50 and 52 via the respective electrical conductors 54, 56 and 58. The switches 48, 50 and 52 are in turn adapted to contact the respective electrical conductors 60, 62 and 64 that are in turn connected to the respective electrode assemblies 22, 24 and 26.

The positive output 46 for the sections 34, 36 and 38 are connected by the conductor 66 to positive skin contacting means comprising a small metal plate member 68 which is adapted to be placed at a suitable location on the skin 70 of the patient whose mouth 18 is undergoing treatment. Such a suitable location might be the chin or the wrist of the patient. It will be noted that each of the respective sections 34, 36 and 38 of the power supply 30 is provided with the respective dial 72, 74 and 76 for varying the output current transmitted to the respective conductors 54, 56 and 58 via the respective connectors 40, 42 and 44.

As illustrated in FIG. 1, means for measuring the current provided to the gingival tissue in the vicinity of a plurality of teeth such as the teeth 12, 14 and 16 in the patient's mouth 18 is provided and is designated generally by the number 78 and comprises a microammeter 80 and associated conductors and switches. The microammeter 80 has three input conductors 82, 84 and 86 that are connected to the respective conductors 54, 56 and 58. The microammeter 80 also has three corresponding output conductors 88, 90 and 92. These conductors 88, 90 and 92 are connected to the respective switches 94, 96 and 98 that are in turn connected to the respective conductors 60, 62 and 64 by the respective conductors 100, 102 and 104.

The switches 94, 96 and 98 are normally open and the switches 48, 50 and 52 are normally closed. However, when it is desired to determine the electric current being supplied to any particular electrode assembly 22, 24 or 26 and hence the gingival tissue contacted by the electrode assembly the proper switch 48, 50 or 52 associated with that electrode assembly is opened and the proper switch 94, 96 or 98 associated with that electrode assembly is closed. For instance, if it were desired to check the current flowing to the electrode assembly 26, the switch 52 would be opened which would disrupt the conduction path between the conductor 64 and 58 via the switch 52. The switch 98 would then be closed to supply a current conduction path between the conductors 58 and 64 via the conductor 86, microammeter 80, conductor 92 switch 98 and conductor 104. When this is accomplished the reading on the milliammeter 80 would indicate how many milliamperes of current were being supplied to the electrode assembly 26 and hence the gingival tissue surrounding the associated tooth 16. If necessary, the current could then be adjusted using the dial 76. The same could be done for the other electrode assemblies 22 and 24.

Figure 2:
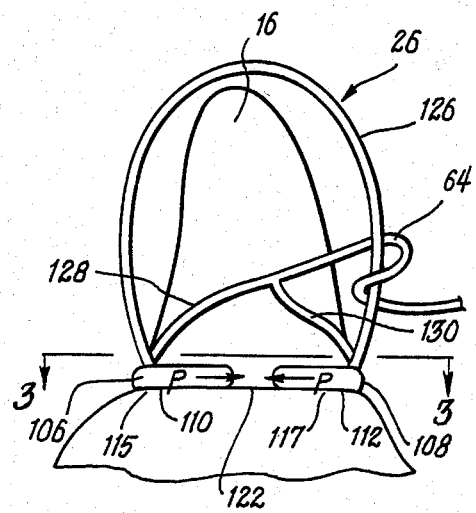
FIG. 2 is an enlarged view of a portion of the structure set forth in FIG. 1 taken generally in the direction of the line 2—2 in FIG. 2.
Figure 3:
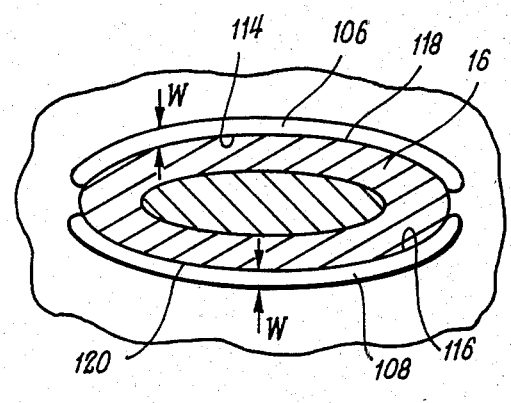
FIG. 3 is a sectional view of the structure illustrated in FIG. 2 taken substantially on the line 3—3 thereof.

FIGS. 2 and 3 illustrate in greater detail the construction of the electrode assemblies 22, 24 and 26. Only the electrode assembly 26 is illustrated in FIGS. 2 and 3 since the construction of the electrode assemblies 22 and 24 is similar to the electrode assembly 26. The electrode assembly 26 comprises two elongated and curved gingival tissue contact members 106 and 108. The respective undersides 110 and 112 of the gingival tissue contact members 106 and 108 are shaped to conform to the shape of the gingival tissue 115 and 117 adjacent the tooth 16. The inner surfaces 114 and 116 of the respective gingival tissue contact members 106 and 108 are shaped to conform respectively to the exterior inner surface 118 and exterior outer surface 120 of the tooth 16 just above the gum line or location 122 on the tooth 16. In the preferred embodiment the width W of the contact members 106 and 108 should be between about 1 to about 2 mm and the length of the contact members should be sufficient to surround substantially 70 to 85 percent of one half of the exterior surface of the tooth 16 when the contact member 106 or 108 is in place on the tooth 16. This description related to the contact members 106 and 108 also applies to the respective contact members 107, 109 and 111 and 113 of the respective electrode assemblies 22 and 14.

As illustrated in FIG. 1, each of the electrode assemblies 22, 24 and 26 has means for holding the respective electrode assemblies on the respective teeth 12, 14 and 16 comprising respective clip members 122, 124 and 126. As best illustrated in FIG. 2 for the electrode assembly 26, the clip members as illustrated for the clip member 126 comprises an elongated bent piece of spring steel that is bent generally into a horse shoe shaped configuration. One end of the clip member 126 is connected to the contact member 106 and the other end is connected to the contact member 108. The slip member 126 is oriented so that it projects upward over and around the top of the tooth 16. The clip member is sized and shaped so that it exerts an inward pressure on the contact members 106 and 108 so that the contact members 106 and 108 exert an inward pressure, designated by the arrows P on the outer surface of the tooth 16 when the electrode assembly 126 is in place on the tooth 16. This description of the clip member 126 and its functioning also apply to the clip members 122 and 124 of the electrode assemblies 22 and 24.

As indicated in FIG. 2, the conductor 64 is wrapped around a portion of the clip member 126 and the end of the conductor 64 is biforcated so that an end portion 128 of the conductor 64 is connected to the contact member 106 and another end portion 130 is connected to the contact member 108. The connections between the contact members 106 and 108 and the conductor portions 128 and 130 are made in a conventional manner such as by soldering or the like.

The apparatus of the invention is made and used and the method of the invention is practiced in the following manner. The contact members 106, 108, 107, 109 111 and 113 are formed from a suitable dental metal so that their inner surfaces conform to the surface of the appropriate tooth 12, 14 or 16 just above the gum line and so that the lower portions conform to the shape of the gingival tissue located adjacent the appropriate tooth 12, 14 or 16 as previously indicated for the contact members 106 and 108. This forming is done in a manner known to those skilled in the art and in a manner in which portions of bridges and braces are formed.

The clip members 122, 124 and 126 are also formed in a manner known to those skilled in the art from suitable spring steel so that they will exert an inward force on the respective contact members 107, 109, 111, 113; and 106, 108 and then the clip members 122, 124 and 126 are heat treated in a manner known to those skilled in the art. Also the ends of the clip members 122, 124 and 126 are welded in a manner known to those skilled in the art to the upper portions of the respective contact members 107, 108, 111, 113; and 106, 108. The appropriate end of the respective conductors 60, 62 and 64 are wrapped around the clip members 122, 124 and 126 and then soldered in a manner known to those skilled in the art to the respective contact members 107, 109; 111, 113 and 106, 108 in the manner previously indicated with respect to the conductor 64 and the contact members 106 and 108 of the electrode assembly 26.

The rest of the circuit illustrated in FIG. 1, including the power supply 30 and the electrical connection means 32 is put together with components known to those skilled in the art and in a manner known to those skilled in the art. In this connection, the power supply 30 can comprise a series of power supplies that provide a variable current in the microampere range that are known in the art. The electrode 68 can comprise any suitable electrical conductor such as a substantially flat or partially curved aluminum conductor. The power supply 30 should be capable of producing a current of between about 5 to 20 microamperes at the contact members 107, 109, 111, 113 and 106, 108 and the associated gingival tissue in the mouth 18. The voltage present between the connectors 40, 42 and 44 and the connector 46 should be between about 5 and about 9 volts DC. Substantially the same voltage should be present between the contact members 107, 109; 111, 113; 106, 108 and the positive contact or electrode 68.

After the circuitry illustrated in FIG. 1 including the power supply 30 and the electrical connection means 32, the microammeter 80 and the electrode assemblies 22, 24 and 26, including the respective contact members 107, 109; 111, 113 and 106, 108, and the respective clip members 122, 124 and 126 have been provided they are used in the following manner. All of the apparatus illustrated in FIG. 1 is brought near the patient and the respective electrode assemblies 122, 124 and 126 are pushed into place on the respective teeth 12, 14 and 16 so that the respective contact members 107, 109; 111, 113 and 106, 108 are firmly seated against the gingival tissue located around each respective tooth 12, 14 and 16. This is, of course, accomplished with all of the switches 48, 50, 52, 94, 96 and 98 being open. The positive metal plate member 68 is then taped into place against the patient's skin 70 at a suitable location such as the chin or wrist.

The treatment is then initiated to the gingival tissue surrounding one or more of the teeth 12, 14 or 16 by closing the appropriate switch 48, 50 or 52. For instance, if it is desired that the gingival tissue near the tooth 14 be treated, then the switch 50 would be closed to permit an electric current to flow from the section 36 of the power supply 30 via the connector 42, the conductor 56, the switch 50, the conductor 62 to the contact members 111 and 113. The current would then flow from the contact members 111 and 113 through the gingival tissue surrounding the tooth 14 in the mouth 18 and any adjacently located bone and through part of the patient's body to the positive contact 68 that is in contact with the patient's skin 70. Current would then flow along the conductor 66 to the section 36 of the power supply 30. The current flowing in the conductor 62 to the contact members 111 and 113 and the gingival tissue adjacent the tooth 14 in the mouth 18 that is in contact with the contact members 111 and 113 can be varied by charging the setting of the dial 74 on the portion 36 of the power supply 30. The current flowing to the gingival tissue in contact with the contact members 111 and 113 can be monitored by opening the switch 50 and closing the switch 96 which causes the electrical current in the conductor 56 to flow to the ammeter 80 via the conductor 84 and then from the ammeter 80 via the conductor 90, switch 96, and the conductor 102 to the conductor 62. The amount of the current will then be read from the ammeter 80. If desired, the current could be monitored in this manner continuously during the treatment. The gingival tissue adjacent the other teeth 12 and 16 can be treated either individually or simultaneously in a similar manner and the same is true for monitoring the current by using the ammeter 80.

In the preferred embodiment the current supplied to the contact members 107, 109; 111, 113 and 106, 108 should be between about 5 to 20 microamperes with about 15 microamperes being preferred. At the same time the voltage between the connectors 40, 42 and 44 and the connector 46 should be between about 5 and about 9 volts DC.

It has been determined that a series of comparatively short treatments produced the best results. In the preferred embodiment the treatment period or the time that electric current is being supplied to the gingival tissue adjacent a tooth 12, 14 or 16 should be from about 8 minutes to about 25 minutes and the heat results for the effort expended were obtained with treatment periods of about 20 minutes. Generally it is desirable to have one treatment a day for several days, with the number of days being dependent upon the severity of the initial defect or disease. If deemed desirable, the patient can operate the equipment at the office or at his or her home.

Although the invention has been described in considerable detail with reference to a certain preferred embodiment, it will be understood that variations and modifications may be made with the spirit and scope of the invention as defined in the appended claims.

What is claimed is:

1. Oral electrical treatment apparatus comprising means for electrically contacting gingival tissue in a mouth, said gingival electrical contacting means comprising at least one electrode assembly including at least two elongated gingival tissue contact members each having an underside shaped to conform to the shape of the gingival tissue adjacent a tooth in said mouth, said gingival tissue contact members each having an inner surface shaped to conform to the exterior outer surface of said tooth just above the gum line, means locatable about said tooth for locating said electrode assembly, and means locatable outside of said mouth for supplying an electrical current to said gingival electrical contacting means.

2. The oral electrical treatment apparatus of claim 1 comprising a plurality of electrode assemblies.

3. The oral electrical treatment apparatus of claim 1 wherein said elongated gingival contact members have a length sufficient to surround substantially 70 to 85 percent of one half of the exterior surface of said tooth when said elongated gingival contact members are in place.

4. The oral electrical treatment apparatus of claim 3 wherein at least a portion of said elongated gingival contact members have a width between about one to about two millimeters.

5. The oral electrical treatment apparatus of claim 3 wherein said means locatable about said tooth for locating said electrode assembly comprises a clip member.

6. The oral electrical treatment apparatus of claim 5 wherein said clip member comprises an elongated bent piece of spring material.

7. The oral electrical treatment apparatus of claim 6 wherein said clip member is sized and shaped to exert an inward pressure on said elongated gingival contact members.

8. The oral electrical treatment apparatus of claim 7 wherein said clip member is bent generally into a horse shoe configuration.

9. The oral electrical treatment apparatus of claim 7 wherein said means for supplying an electrical current also includes means for varying the output current therefrom.

10. The oral electrical treatment apparatus of claim 9 further comprising means for monitoring the electrical current received by the gingival tissue from said electrical contacting means.

11. A method of treating disease or defects in the mouth having teeth comprising: providing a plurality of electrical contacts for contacting gingival tissue in said mouth, said electrical contacts having an inner surface conforming to the surface of a tooth just above the gum line and having lower portions conforming to the gingival tissue located adjacent to the tooth; means for locating and exerting a pressure on said electrical contacts to contact gingival tissue around a tooth in said mouth; and means for supplying an electrical current to said plurality of electrical contacts; placing said locating and pressure exerting means and electrical contacts in said mouth with the contacts surrounding a substantial portion of a tooth to cause said electrical contacts to contact said gingival tissue surrounding said tooth and activating said means for supplying an electrical current to supply electrical current to said electrical contacts and to said gingival tissue surrounding said tooth.

12. The method of claim 11 further comprising supplying means for adjusting the electrical current supplied by said electrical current supply means and using said adjusting means to adjust the current supplied by said electrical current supplying means.

13. The method of claim 12 further comprising providing means for monitoring the electrical current to the gingival tissue through said electrical contacts and using said electrical current monitoring means for monitoring the current supplied to said gingival tissue.

14. The method of claim 12 wherein said step of supplying an electrical current to said electrical contacts comprises supplying a current between about five microamperes and about twenty microamperes.

15. The method of claim 14 wherein the step of supplying an electrical current to said electrical contacts comprises supplying a current of about fifteen microamperes.

16. The method of claim 12 wherein said step of activating said means for supplying an electrical current comprises supplying electric current for a period of time from about eight to about twenty-five minutes.

17. The method of claim 16 wherein said step of activating said means for supplying an electrical current comprises supplying an electrical current for a period of time of about twenty minutes.

* * * * *